United States Patent [19]

Huggins

[11] 4,034,773
[45] July 12, 1977

[54] METHOD AND APPARATUS FOR METERING FLUIDS

[76] Inventor: James A. Huggins, 551 W. Park Ave., Libertyville, Ill. 60048

[21] Appl. No.: 601,089

[22] Filed: Aug. 1, 1975

Related U.S. Application Data

[63] Continuation-in-part of Ser. No. 423,387, Dec. 10, 1973, abandoned, which is a continuation-in-part of Ser. No. 320,242, Jan. 2, 1973, abandoned.

[51] Int. Cl.² .......................................... F16K 7/06
[52] U.S. Cl. .................................. 137/1; 24/134 R; 137/382; 251/9
[58] Field of Search .............. 251/4, 6, 9; 137/377, 137/382, 1; 24/132 HA, 134 R; 222/556

[56] References Cited

U.S. PATENT DOCUMENTS

| | | | |
|---|---|---|---|
| 3,102,710 | 9/1963 | Dresden | 251/9 |
| 3,215,394 | 11/1965 | Sherman | 251/4 |
| 3,685,787 | 8/1972 | Adelberg | 251/6 |
| 3,813,077 | 5/1974 | Kolic | 251/9 |
| 3,893,468 | 7/1975 | McPhee | 251/6 X |

Primary Examiner—Martin P. Schwadron
Assistant Examiner—Richard Gerard
Attorney, Agent, or Firm—Olson, Trexler, Wolters, Bushnell & Fosse

[57] ABSTRACT

A clamp and related method provides for a stable fluid flow rate through a flexible tubing. The clamp comprises a body having an anvil and a tube-constricting cam that cooperates with the anvil to pinch together diametrically opposed sections of the tubing to provide a reduced flow passageway. The cross-sectional area of this passageway, and hence the fluid flow rate, is varied by rotating the cam to change the transverse extent of the pinched off portions. The reduced flow passageway is constrained at each adjustment of the clap to prevent variations in flow rate due to displacement of the material of the tubing wall.

15 Claims, 11 Drawing Figures

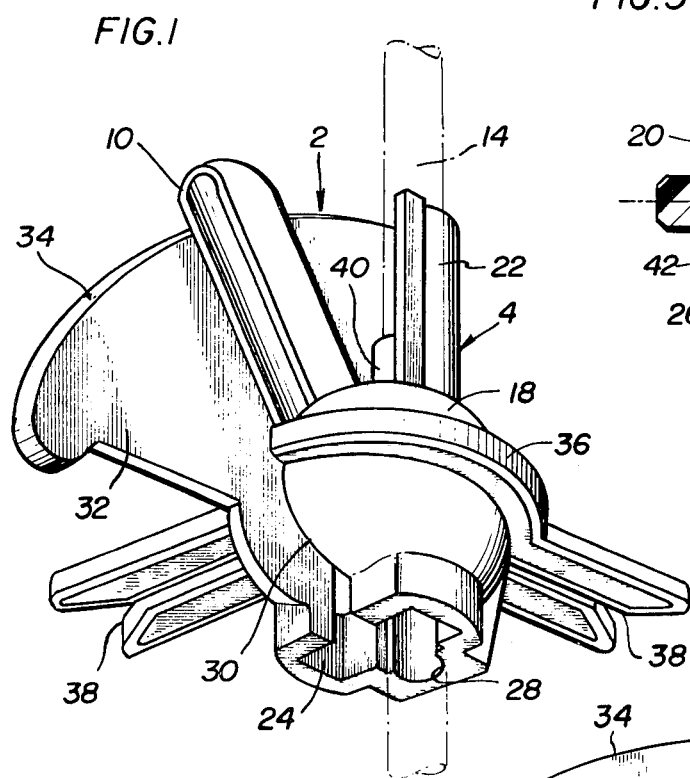
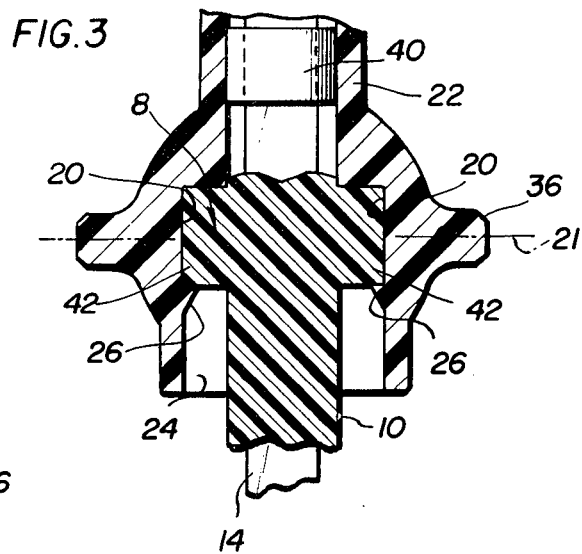
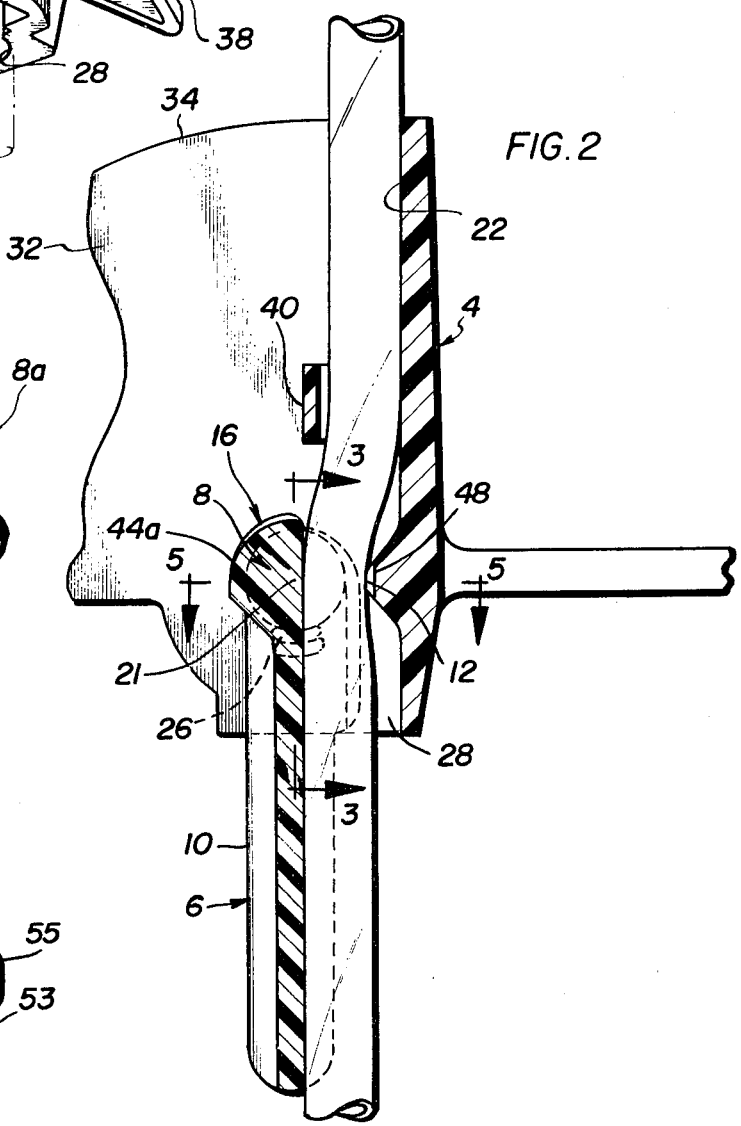
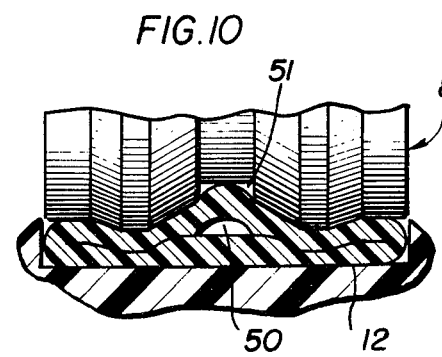
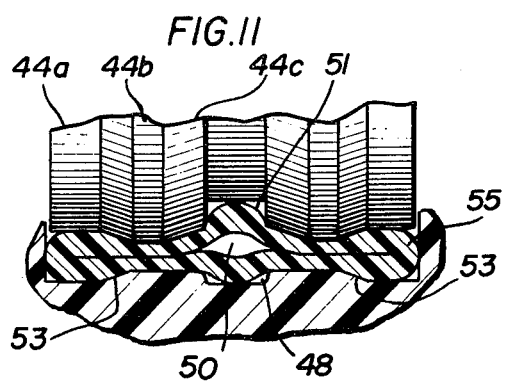

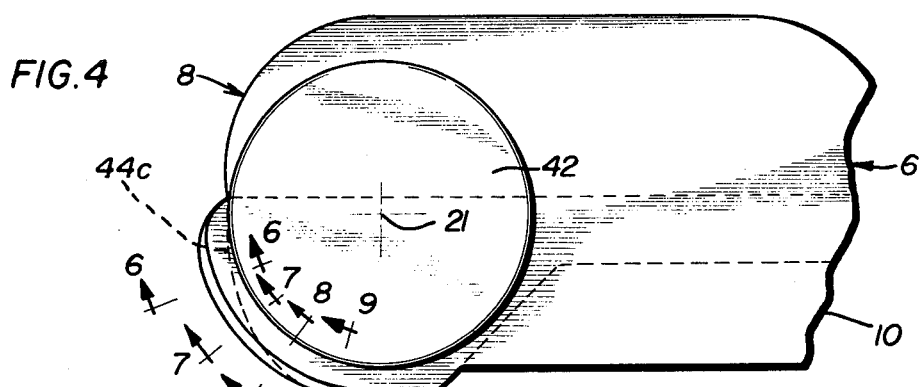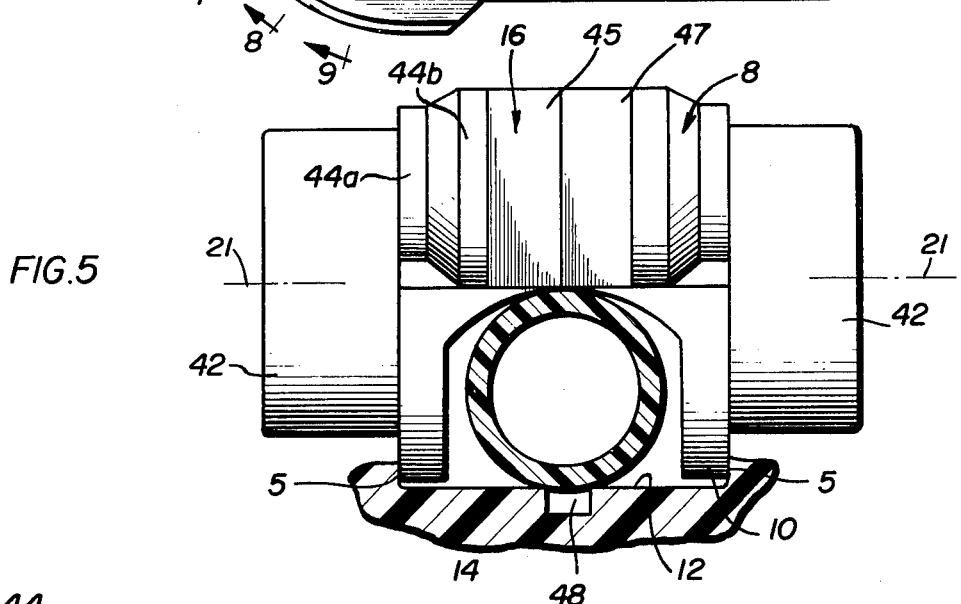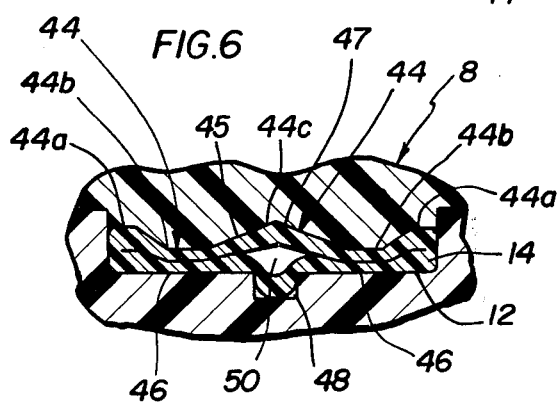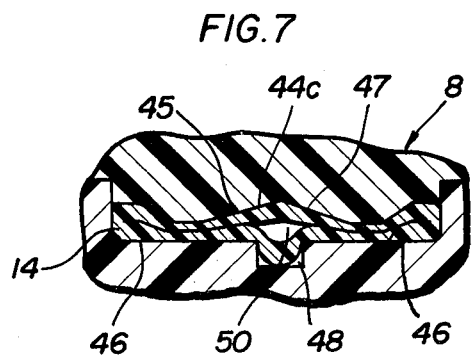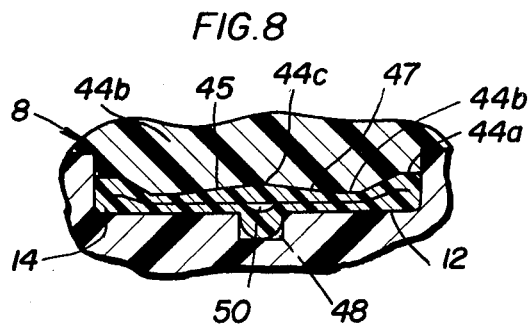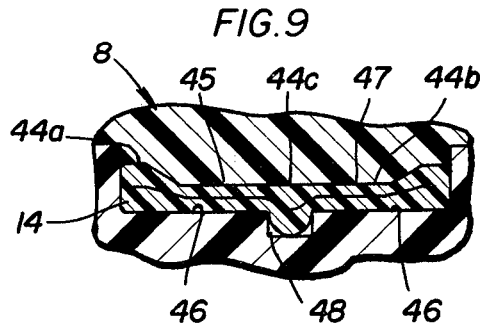

METHOD AND APPARATUS FOR METERING FLUIDS

CROSS REFERENCE TO RELATED APPLICATIONS

This application is a continuation-in-part of my copending application Ser. No. 423,387, filed Dec. 10, 1973, now abandoned which is, in turn, a continuation-in-part of my application Ser. No. 320,242 filed Jan. 2, 1973 and now abandoned. The entire disclosures of each of said applications are by reference incorporated herein.

BACKGROUND OF THE INVENTION

This invention relates to adjustable clamps and methods for controlling the rate of fluid flow through flexible plastic tubing such as used for intravenous infusion of liquid nourishment and/or medication. The intravenous infusion of medicinal fluids is quite common in current medical practice. Anesthetics are infused intravenously during operations, and intravenous feeding is commonly employed in the post-operative period. In addition, there are many patients whose illness either restricts their ability to take food orally or to digest food properly so taken, and then patients must be fed intravenously for the duration of their illness.

The apparatus commonly employed for intravenous infusions includes a stand for supporting a bottle of the appropriate fluid in an elevated position above the patient. A flexible plastic tube is coupled to the bottle for conducting the fluid from the bottle to the patient by a gravity feed. A needle on the end of the flexible tube is inserted into one of the patient's veins, and an adjustable clamp on the tubing is used for controlling the flow rate of the fluid by controlling the cross sectional area of the tubing. In order to measure the flow rate with these devices it is necessary to count visually the number of drops per minute by watching the drops in a drip chamber.

In the past, a problem has been encountered in maintaining a constant fluid flow rate through the flexible plastic tubing (usually polyvinylchloride) because of its physical characteristics. After the desired fluid flow rate has been set with the adjustable clamp, as by restricting a portion of the cross-section of the tubing, the plastic wall of the tubing nevertheless tends to deform or displace slowly resulting in a progressive change in the cross sectional area through which the fluid is flowing, thereby progressively changing the fluid flow rate through the tubing. This requires frequent readjustment of the clamp in order to make sure that the correct fluid flow rate is maintained. Tests have shown that the standard intravenous set loses an average of 45% of its initial flow rate in ten minutes if not readjusted.

OBJECTS AND SUMMARY OF THE INVENTION

A principal object of this invention is to provide for accurately controlling the flow rate through a length of flexible tubing. In general this is accomplished by a method and apparatus which involves clamping the tubing in such a manner that the cross sectional area within the tubing for fluid flow is effectively prevented from changing, once having been set, by the use of proper clamping and constraining forces on the tubing and by localizing the areas of these forces.

In the method of this invention the tubing is pinched shut laterally in two opposed zones leaving a central region or passageway which is regulated from full on to full off and various drip rates therebetween. Each of the two opposed zones is subdivided into an end or outer region at which the tubing is pinched or compressed shut but avoiding rupture of the tube, and an inner region at which the tubing is compressed to less than the combined thickness of the two walls that are pressed together and sufficient to prevent subsequent change of the cross section of said passageway.

The clamp of the invention comprises means such as an anvil that forms a narrow surface for receiving a portion of the tubing to support the same. The clamp also has tube-constricting means in the form of a lever-operated, relatively small, rotatable cam. The cam has first portions cooperating with first parts of the anvil or surface for providing opposed structures that compress diametrically opposed wall portions of the tubing an amount sufficient to shut off the tubing at spaced regions. The opposed structures are shaped to apply sufficient pressure to the tubing to reduce the wall thickness of the tubing. The tube-constricting means also has second portions cooperating with a second part of the anvil or surface for providing structure defining a space for a reduced-flow passageway in the tubing. The structure that defines a space for the reduced flow passageway is located between the opposed structures. Also, said opposed structures and the structure defining the space for the reduced flow passageway provide a substantial confinement for the tubing extending almost completely around the tubing. The tube-constricting means includes an arm structure pivotal relative to said anvil surface, and in addition spaced peripheral parts which constitute the aforesaid first portions. The cross-sectional area of the reduced flow passageway in the tubing varies in accordance with the position of the arm structure, which is manually operated.

BRIEF DESCRIPTION OF THE FIGURES

FIG. 1 is a perspective view of a clamp constructed in accordance with and embodying the present invention;

FIG. 2 is a vertical sectional view of the clamp of FIG. 1 taken substantially through the longitudinal center line of the cam lever and the longitudinal center line of the tube but showing the cam arm and cam rotated from the position of FIG. 1 to the full open position;

FIG. 3 is an enlarged fragmentary sectional view taken along line 3—3 of FIG. 2;

FIG. 4 is an enlarged fragmentary side elevational view of the cam lever and the cam that is at one end thereof;

FIG. 5 is an enlarged fragmentary sectional view taken along line 5—5 of FIG. 2 in the full open position;

FIG. 6 is a fragmentary sectional view taken approximately along line 6—6 of FIG. 4 but showing the cam assembled with the body and rotated to a position such that line 6—6 is normal to the anvil, and the tubing is partially constricted;

FIG. 7 is a view similar to FIG. 6 and showing a further rotated position of the cam and as seen from line 7—7 of FIG. 4 and wherein the tubing is constricted to permit trickle of fluid to flow therethrough;

FIG. 8 is a view similar to FIG. 6 and showing a further rotated position of the cam as seen from line 8—8 of FIG. 4 and in which the flow through the tubing will be at a low drip rate;

FIG. 9 is a view similar to FIG. 6 and showing still another rotated position of the cam as seen from line 9—9 of FIG. 4 and in which the tubing is completely shut off;

FIG. 10 shows a modified form of the invention; and

FIG. 11 shows a still further modified form of the invention.

DETAILED DESCRIPTION

Referring now in more detail to the drawings there is shown a clamp 2 having a body 4 in which there is positioned an arm structure 6 comprising generally a cam 8 and an arm or lever 10. Generally speaking, the body 4 rotatably supports the cam 8, the latter being rotated by manipulation of a lever 10 to which it is integrally connected. The body 4 has a tube-supporting surface or anvil 12 that receives the plastic tubing 14, and the peripheral surface 16 of the cam 8 cooperates with the anvil 12 to constrict the tube thereby to vary the flow rate therethrough from substantially full flow to complete shut off, as will be presently more fully described. The width of the anvil surface 12 between side walls 5,5 (FIG. 5) is approximately the same as the width of the tubing when flattened. The dimension of the anvil surface 12 at right angles to said width should be narrow but not so narrow as to approach a knife edge that would cut the tube. Preferably said dimension is approximately the same as twice the wall thickness of the tube.

The body 4 further comprises a central bulb-like housing portion 18 having opposed cylindrical sockets 20,20 and a generally U-shaped channel 22 extending from the region of the socket 20,20 outwardly of the housing portion 18. Opposite from the channel 22 the housing portion 81 has an opening 24 which terminates adjacent to the sockets 20, 20 in retaining lips 26, 26. The opening 24 also has a generally arcuate section 28 for receiving a portion of the tube, as best seen in FIGS. 1 and 2, when the clamp is mounted on the tube.

Also formed in the housing portion 18 is a slot 30 which extends approximately 180° to provide clearance for the lever 10, enabling the latter also to move approximately 180°. The slot 30 is bounded on one side by a guard or shield 32 which extends approximately 90° arcuately as best seen in FIG. 1. The shield 32 also extends outwardly to a periphery 34 which is slightly short of the radial extent or free end of the lever 10. The shield 32 preferably constitutes an extension of one wall of the channel 22 and at its radially inner end is integral with the housing portion 18. The shield helps to prevent accidental movement of the lever 10 over the 90° of movement that is most critical and which will be generally used in intravenous feeding.

Centrally thereof the housing portion 18 is integrally formed with a stiffening flange structure 36 from which there are two groups bifurcated radial projections 38, 38. Each pair of projections 38 provide a temporary tube shut-off structure to be used when changing intravenous solution bottles. Thus, an intravenous supply tube, like the tube 14, can be inserted into the slot between each pair of projections 38 to constrict the tube to shut it off temporarily. For example, this may be done with a dual bottle apparatus using a Y fitting to supply a single tube that delivers fluid to the patient. Each bottle can be shut off separately or at the same time.

Within the channel 22 and spaced from the sockets 20, 20 the body 4 integrally includes a guide 40 which serves to retain the tubing 14 in the channel 22. The guide 40 also aids in assembling the tube 14 with the clamp 2 because the guide 40 guides the tube 14 into the space between the anvil 12 and the cam periphery 16, as best seen in FIG. 2. In assembling the tube 14 with the clamp, the tube is passed through the openings 24, 28 with the lever 10 and cam 8 in the full open positions shown in FIGS. 2 and 5. The tube will assume a slight bend near the anvil 12. The guide 40 helps prevent the clamp from sliding on the tube when the clamp is fully open as in FIG. 2.

In the form of the invention herein shown, the body 4 and the arm structure or cam-lever unit 6 constitute two molded plastic pieces that make up the clamp. The plastic may be a high density polyethylene, but other plastics may be used. The two plastic pieces are sufficiently yieldable elastically so that they may be readily assembled. This reduces the manufacturing costs of the clamp.

Referring again to the cam 8 it will be seen that it has opposed trunnions 42, 42 which are of cylindrical configurations and which are shaped to fit slidably and conformably (but with some friction) in the sockets 20, 20. The trunnions 42, 42 thus rotate about an axis 21 which is generally transverse to the longitudinal axis of the tubing 14. The opening 24 is sized for receiving the trunnions 42, 42 during assembly of the cam with the housing portion 18. As the trunnions 42, 42 are moved past the lips 26, 26, the latter are caused to distend but they snap back into their normal positions when the trunnions 42, 42 have become seated in the sockets 20, 20. The lips 26, 26 thus retain the cam 8 assembled with the housing portion 18.

The peripheral tube-constricting surface 16 of the cam 8 is uniquely designed to cooperate with the anvil 12 to control the flow of fluid in the tubing 14. The axis 21 of the cam 8 is the axis of rotation of the trunnions 42; however, certain portions of the cam surface 16 are eccentric to the axis 21 as will hereinafter be described. The rotational position of the cam 8 determines the flow rate through the tubing.

FIGS. 6 – 9 show positions of the cam in the last 90° of movement, i.e. where the lever 10 is in the region of the shield 32. The cam 8 has first peripheral portions 44, 44 cooperating with first parts 46, 46 of the anvil surface to pinch shut diametrically opposed portions of the tubing 14 on opposite sides of the longitudinal axis of the tubing. In the outer regions 44a, 44a the tubing wall is pinched shut and constricted to slightly less than the normal wall thickness. Overconstricting the tube at the regions 44a should be avoided in order to prevent tube rupture. In the regions 44b, 44b the tubing wall is preferably compressed to about one-half its normal thickness. Central region 44c forms a second portion of the cam periphery that cooperates with a second part or groove 48 of the anvil to define a confinement structure for a reduced flow passageway 50 of the tubing. The tubing is thus pinched shut except at the passageway 50 where the tubing is confined to prevent displacement and consequent change in cross-sectional area. Thus the flow rate is maintained as adjusted.

At various angular positions about the cam axis central region 44c has its surface portions 45, 47 at varying distances from the axis of rotation 21 of the cam 8 while the end regions 44a, 44b have their respective surface portions at constant distances from the axis of rotation 21 of the cam. The result is that the central region 44c forms a cavity which tends to flatten out or become shallower as the cam is rotated from a tube-open position shown in FIG. 6 through the trickle position of FIG. 7 and the slow drip position of FIG. 8 to a tube fully-closed position shown in FIG. 9 while the tube at the region 44a remains confined to a relatively constant extent. During such cam movement the regions 44b, 44b that are presented against the tubing become progressively wider. Viewed another way, the angle formed by the surfaces 45, 47 become less and less obtuse as the cam is rotated from the tube-closed position shown in FIG. 9 to the position of FIG. 6 resulting in the cavity formed by the surfaces 45, 47 pulling away from the tubing to allow the size of passageway 50 to increase. When the condition of FIG. 9 is reached, the cam surface that is presented toward the tubing is substantially flat, that is surface portions 45, 47 form approximately a straight angle.

The groove 48 is preferably of rectangular cross section. The groove 48 serves to confine the reduced flow passageway 50 to aid in preventing changes in the cross-section of the passageway due to displacement of the tubing wall once the flow rate has been set by the position of the cam 8.

The lever operated cam 8 provides a first class lever with substantial mechanical advantage that facilitates application of the necessary constricting and confining forces to the tubing. The lever 10 operates in conjunction with the surfaces 45, 47 that converge in a direction generally toward the axis of rotation 21 of the cam to provide a recess of varying depth for confining the reduced flow passageway 50.

FIG. 10 shows a modified form of the invention in which the groove or recess 48 is eliminated from the anvil 12 and instead is formed as a groove 51 in the cam 8a. This groove 51 will be located centrally of the cam 8a, that is in the region of juncture of the surfaces 45, 47. Otherwise, the arrangement in FIG. 10 is the same as that in FIGS. 1-9.

FIG. 11 is a further modified form of the invention in which the difference lies in the fact that grooves 51 and 48 are in both the cam and in the anvil. The groove 51 need only be very shallow, for example, of the order of a few thousands of an inch. The anvil surface may be as in FIGS. 1 – 10 or the anvil surface may have a shoulder or step 53 at each side to relieve the side quadrants 55 of the tubing to prevent overstressing thereof.

The invention is claimed as follows:

1. A clamp for providing a stable fluid flow rate through a flexible tubing, said clamp comprising means forming a surface for receiving a portion of said tubing and supporting the same, and tube constricting means having first portions cooperating with first parts of said surface for providing opposed structures that compress diametrically opposed wall portions of the tubing an amount sufficient to shut off the tubing at spaced regions, and said constricting means also having means cooperating with a second part of said surface for providing structure defining a space for a reduced-flow passageway in the tubing, said opposed structures and said first portions being shaped to apply sufficient pressure to the tubing to reduce the wall thickness of the tubing, said structure defining the space for said reduced flow passageway being between said opposed structures, said opposed structures and the structure defining said space together providing a substantial confinement for the tubing extending around the tubing, and said constricting means including arm structure pivotal relative to said surface and including spaced peripheral parts constituting said first portions, said spaced peripheral parts being of such shape that upon pivoting of said arm structure to reduce fluid flow through said passageway said peripheral parts present progressively greater areas against said tubing to increase the extent of each of said spaced regions transversely of the tubing, and said first parts being relatively narrow to restrict said regions to narrow bands transversely of the tubing.

2. A clamp according to claim 1 in which the distance from the axis of said pivotal structure to at least one of said peripheral portions is variable so that rotation of said arm structure about said axis varies the amount of constricting pressure on said tubing and also varies the cross-sectional area of said reduced flow passageway.

3. A clamp according to claim 2 in which arm structure comprises a first class lever.

4. A clamp according to claim 1 in which said opposed structures and said first portions are shaped so as to compress the tubing wall to about one-half is normal thickness.

5. A clamp according to claim 1 in which the narrow bands are each approximately twice the wall thickness of said tubing.

6. A clamp for providing a stable fluid flow rate through a flexible tubing, said clamp comprising a body having means including an anvil for receiving and supporting a portion of said tubing, a cam rotatable in said body about a substantially fixed axis generally transverse to the longitudinal axis of said tubing portion, said cam having opposed peripheral portions on opposite sides of the longitudinal axis of said tubing portion, said peripheral portions having tube-constricting surfaces cooperating with said anvil to shut off diametrically opposed portions of said tubing portion, said anvil being relatively narrow in the direction transverse to said tubing, said cam and said anvil having cooperating portions between said tube-constricting surfaces that define a space for receiving and confining a reduced flow passageway of said tubing portion, said tube-constricting surfaces having sections thereof at varying radial distances from the axis of rotation of the cam and shaped to present tube-constricting surfaces of varying dimensions transversely of the tubing to vary the extent of the shut off portions transversely of the tubing and thereby vary the cross-section of said reduced flow passageway in accordance with various positions of said cam.

7. A clamp according to claim 6 in which said tube-constricting surface sections converge in a direction generally toward said axis of rotation to provide a recess of varying depth that in part receives said reduced flow passageway, said recess diminishing to a minimum depth at a region at which the cam cooperates with the anvil to close completely the reduced flow passageway.

8. A clamp according to claim 7 in which said recess includes a groove in said cam, and there is a groove in said anvil which in part receives said reduced flow passageway.

9. A clamp according to claim 7 in which there are end surface sections adjacent to the recess for engaging the flattened longitudinal margins of the tube, said end surface sections remaining at a substantially constant distance from said axis at various positions of orientation of the cam about said axis.

10. A clamp according to claim 6 in which said space for said reduced flow passageway is in part defined by a groove in said anvil.

11. A clamp according to claim 6 in which said space for said reduced flow passageway is in part defined by a groove in said cam.

12. A clamp according to claim 6 in which said reduced flow passageway is defined by grooves in the anvil and in the cam.

13. A clamp for providing a stable fluid flow rate through a flexible tubing, said clamp comprising a body having a narrow supporting surface adapted to run transversely of and support a portion of said tubing, a cam rotatable about an axis passing through said body in said body, said cam and said supporting surface providing cooperating means for constricting portions of the tubing while leaving a confined reduced flow passageway, said cooperating means comprising cam surfaces on said cam, said cam surfaces being of varying radial distances from said axis, said cam surfaces also converging in a direction toward said axis to provide a recess presented toward said narrow supporting surface, the depth of said recess presented toward said surface varying in accordance with the orientation of said cam, said cam having a lever for effecting rotation of the cam, and a shield integral with said body and extending along side of said lever throughout substantially the radial extent of said lever and also throughout a substantial arc of travel of said lever.

14. A method of controlling the fluid flow rate through a reduced flow passageway in length of flexible plastic tubing in such a manner as to minimize flow rate variations in said passageway due to variations in cross-sectional area thereof resulting from displacement of the material of the tubing, said method comprising the steps of constraining a section of the tubing in a path that extends completely around the circumference of said tubing, and laterally pinching two diametrically opposed portions of the tubing together by a force exerted from the outside in and within said constrained path to shut said tubing at said pinched portions and provide said reduced flow passageway between said two shut portions and with the opposed portions being restricted to relatively narrow zones transversely of the tube, the constrained path being such as to prevent significant displacement of the tubing and the pinching forces being of sufficient magnitude that the tubing in at least a part of each of said opposed portions is reduced in wall thickness and remains closed at said opposed portions over comparatively long periods of time, and varying the cross-sectional area of said passageway in a selected manner to vary the fluid flow therethrough, said varying being effected by increasing or decreasing the extent of said opposed pinched portions transversely of the tubing; and in which each of said opposed portions comprises an inner region adjacent an end region, and pinching said inner region shut to an extent that is greater than that of said end region.

15. A method according to claim 14 in which said reduced wall thickness is less than about one-half of the normal tube wall thickness.

* * * * *